United States Patent
Schoedel et al.

(10) Patent No.: US 6,204,399 B1
(45) Date of Patent: Mar. 20, 2001

(54) PROCESS AND ARRANGEMENT FOR PRODUCING TETRAHYDROFURAN

(75) Inventors: Nicole Schoedel, Munich; Ernst Haidegger, Hoehenkirchen; Karl-Heinz Hofmann, Germering, all of (DE)

(73) Assignee: Linde Aktiengesellschaft (DE)

( * ) Notice: Subject to any disclaimer, the term of this patent is extended or adjusted under 35 U.S.C. 154(b) by 0 days.

(21) Appl. No.: 09/101,709
(22) PCT Filed: Jan. 10, 1997
(86) PCT No.: PCT/EP97/00103
  § 371 Date: Jul. 16, 1998
  § 102(e) Date: Jul. 16, 1998
(87) PCT Pub. No.: WO97/26255
  PCT Pub. Date: Jul. 24, 1997

(30) Foreign Application Priority Data

Jan. 16, 1996 (DE) .............................................. 196 01 375

(51) Int. Cl.[7] .................................................. C07D 303/38
(52) U.S. Cl. ............................................ 549/509; 422/187
(58) Field of Search .............................. 549/509; 422/187

(56) References Cited

U.S. PATENT DOCUMENTS

| 4,124,600 | 11/1978 | Jenkins, Jr. ........................... 549/509 |
| 4,196,130 | 4/1980 | Huchler et al. ......................... 203/29 |
| 4,383,895 | 5/1983 | Ernst et al. ........................... 568/868 |
| 4,419,189 | 12/1983 | Caracciolo ............................. 203/77 |
| 5,209,825 | 5/1993 | Badat et al. ........................... 203/29 |

FOREIGN PATENT DOCUMENTS

| 2461922 | 7/1976 | (DE) . |
| WO 96/14281 | 5/1996 | (EP) . |
| 7-053424 | * 2/1995 | (JP) . |

\* cited by examiner

*Primary Examiner*—Bernard Dentz
(74) *Attorney, Agent, or Firm*—Evenson, McKeown, Edwards & Lenahan, P.L.L.C.

(57) ABSTRACT

Process and arrangement for producing tetrahydrofuran from a hydrous butane diol solution contaminated by light volatile, organic compounds, comprising the following process stages:

a) Distillative removal (K1) of the light volatile, organic compounds contained in the hydrous butane diol solution 1.

b) Dehydrating (R) of the thus prepurified hydrous butane diol solution 3 over an acidic aluminum oxide catalyst.

c) One-step or multi-step distillation (K2) of the thus obtained high-tetrahydrofuran fraction 8 for obtaining a pure tetrahydrofuran.

In addition, a separation of the water from the hydrous butane diol solution to water contents of from 2 to 70% by weight, particularly 2 to 10% by weight, can take place before the dehydrating of the butane diol.

13 Claims, 1 Drawing Sheet

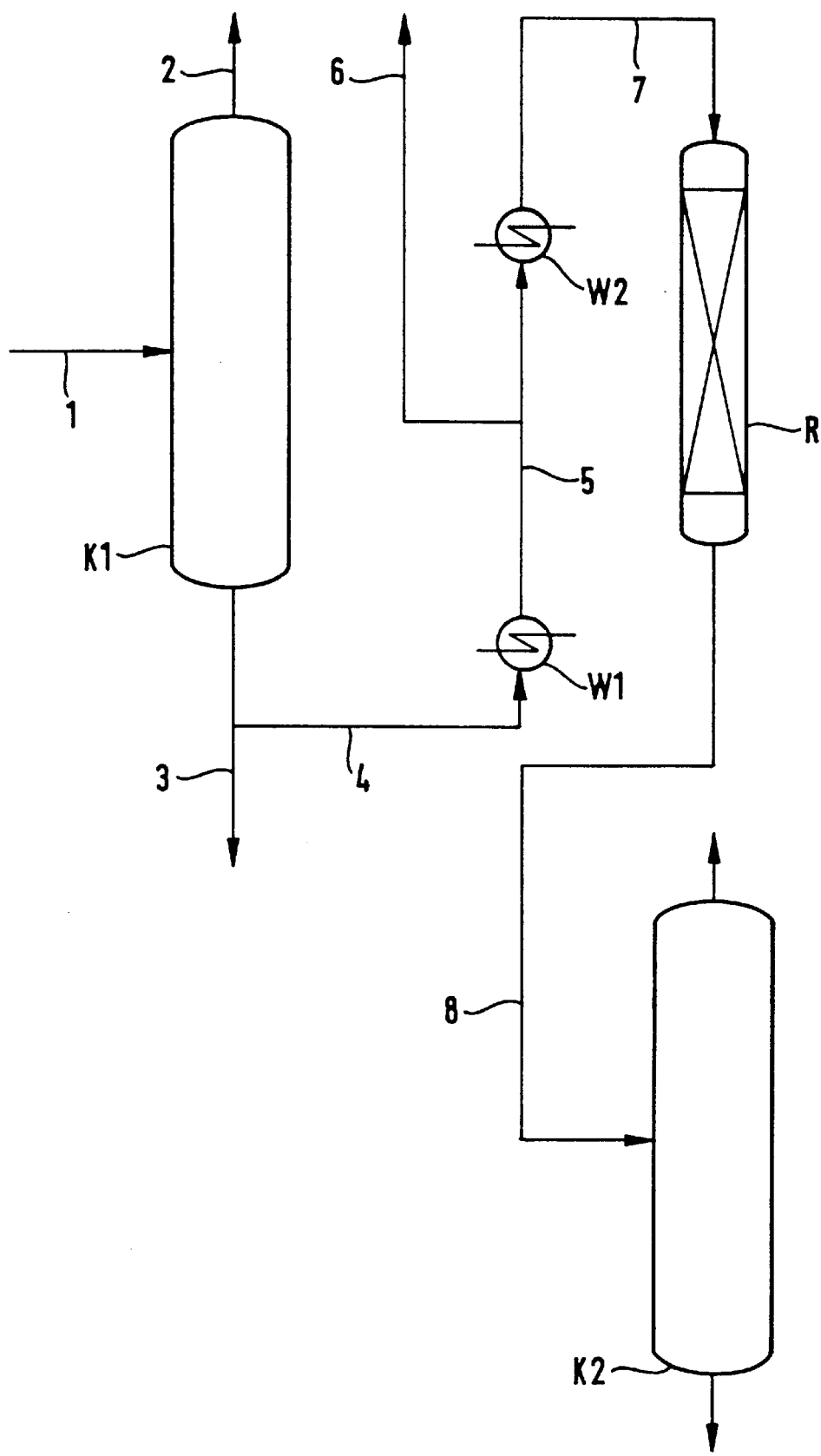

PROCESS AND ARRANGEMENT FOR PRODUCING TETRAHYDROFURAN

This application is a 371 of PCT/EP97/00103, filed Jan. 10, 1997.

BACKGROUND AND SUMMARY OF THE INVENTION

The invention relates to a process and to an arrangement for producing tetrahydrofuran from a hydrous butane diol solution contaminated by light volatile organic compounds.

Processes for producing tetrahydrofuran from hydrous butane diol solutions have been known for some time.

The mentioned processes for producing tetrahydrofuran from a hydrous butane diol solution have in common that the hydrous raw butane diol solution, which as a rule contains approximately 20 to 50% butane diol in water, is first purified in a multistage distillation from undesirable low-boiling and high-boiling constituents, including water. Subsequently, the now anhydrous pure butane diol is catalytically converted on a packed-bed catalyst to tetrahydrofuran and water. The tetrahydrofuran product solution containing water and other low-boiling and high-boiling constituents is subsequently processed again in several stages in a distillative manner to pure tetrahydrofuran.

From German Patent Document DE-OS 25 09 968, a process is known for producing tetrahydrofuran in which the hydrous raw butane diol solution is dehydrated in the liquid phase. As dehydration catalysts, inorganic acids, such as $H_2SO_4$ or $H_3PO_4$ are used. However, these inorganic acids are difficult to handle because they cause, for example, increased corrosion, and their disposal presents problems.

Another process for producing tetrahydrofuran is the so-called Reppe process. In the Reppe process, the conversion of hydrous butane diol solution takes place by way of an acidic catalyst, as a rule $H_3PO_4$, in the liquid phase at temperatures of above 250° C. and pressures of approximately 100 bar. To implement this process requires the lay-out of a reactor or reactors to obtain high pressure, as well as corresponding condenser units. In addition, the process results in significant quantities of undesirable by-products which, on the one hand, have a gluing effect on the acidic catalyst and, on the other hand, cannot be separated or can only be separated poorly. A detailed description of the Reppe process can be found, for example, in *BIOS-Report* No. 367 (1945), FIG. 14.

The above-mentioned processes for producing tetrahydrofuran from a hydrous butane diol solution have in common that the hydrous raw butane diol solution, which as a rule contains approximately 20 to 50% butane diol in water, is first purified in a multi-stage distillation—partly in vacuum columns requiring high investment and operating costs—from undesirable low-boiling and high-boiling constituents, including water. Subsequently, the now anhydrous pure butane diol is catalytically converted on a packed-bed catalyst to tetrahydrofuran and water. The tetrahydrofuran product solution containing water and other low-boiling and high-boiling constituents is subsequently processed again in several stages in a distillative manner to pure tetrahydrofuran. Since, in the known process corresponding compounds are formed again, during the hydration of butane diol comparable purifying or separating steps are carried out twice.

As far as the process is concerned, these required purification and separation steps require comparatively high expenditures because they each consist of several distillation columns arranged behind one another. In addition to high operating and investment costs, this process has an additional disadvantage that, because of thermal stress during the individual distillation steps and a loss of catalyst selectivity in the anhydrous state, there is an increased occurrence of by-products, which results in tetrahydrofuran product losses.

Those processes for producing tetrahydrofuran which avoid such high-expenditure purification and separation steps, as a rule, work with free acids, which is unfavorable economically as well as with respect to protecting the environment. For example, requirements include: a high-expenditure reactor concept, corrosion problems must be taken into account and acid removal or neutralization requires at least one additional purification step. Acid waste disposal is also a problem.

It is an object of the present invention to provide a process and arrangement for producing tetrahydrofuran, in which the above-mentioned disadvantages can be avoided and the overall expenditures for such a system can therefore be reduced.

According to the invention, this is achieved in that a) light volatile organic compounds contained in the hydrous butane diol solution are removed by distillation;

b) then the thus prepurified hydrous butane diol solution is dehydrated over an acidic aluminum oxide catalyst; and c) the thus obtained high-tetrahydrofuran fraction is distilled in one or more stages for obtaining pure tetrahydrofuran.

As mentioned initially, the invention also relates to an arrangement for producing tetrahydrofuran from a hydrous butane diol solution contaminated by light volatile organic compounds.

For achieving the above-mentioned object of the invention, an arrangement is suggested which has a) at least one distillation column for removing light volatile organic compounds from a hydrous butane diol solution;

b) a reactor (R) connected behind the distillation column(s), particularly a packed-bed reactor, in which dehydration of hydrous butane diol solution to a high-tetrahydrofuran fraction takes place; and c) an after purification system, which distills in one or more stages, and is used for obtaining pure tetrahydrofuran from the high-tetrahydrofuran fraction drawn from the reactor.

BRIEF DESCRIPTION OF THE DRAWINGS

The invention as well as further developments of the invention which represent the objects of subclaims will be explained in detail in the following by means of the FIGURE.

By way of line 1, a hydrous butane diol solution contaminated with light volatile organic compounds is fed to the distillation column K1. The water content of the hydrous butane diol solution amounts to 1 to 95% by weight $H_2O$, preferably 10 to 90% by weight $H_2O$, particularly 40 to 70% by weight $H_2O$. The water content depends on the history or the production process of the butane diol solution.

According to a further development of the process of the invention, the distillative separation of the light volatile organic compounds from the hydrous butane diol solution takes place at an essentially normal pressure and at a temperature of from 70 to 150° C., particularly at a temperature of from 90 to 120° C.

The term "column operated essentially at a normal pressure" means that a slight underpressure as well as overpressure can be implemented in the distillation column and may be intended.

By way of line 2, the light volatile organic compounds removed by distillation from the hydrous butane diol solution are drawn at the head of this distillation column K1. By way of line 3, a hydrous butane diol solution largely freed of light volatile organic compounds is drawn at the bottom of the distillation column K1. The portion of this hydrous butane diol solution which is not fed to the reactor R by way of lines 4, 5 and 7 can be processed, for example, to pure butane diol.

The portion of the hydrous butane diol solution which is used for producing tetrahydrofuran is fed by way of line 4 to a first heat exchanger W1. In this heat exchanger W1, a heating of the hydrous butane diol solution by approximately 20 to 50° C. takes place against a heating medium, such as water (vapor). The water vapor occurring during this warming-up can be drawn off by way of line 6. By way of line 5, the already partially dehydrated hydrous butane diol solution is fed to a second heat exchanger W2, in which a heating of the hydrous butane diol solution to 220 to 300° C. again takes place against a heating medium.

According to an advantageous embodiment of the process of the invention, separation of the water from the hydrous butane diol solution takes place before the dehydrating of the butane diol to water contents of from 2 to 70% by weight water, particularly 2 to 10% by weight water.

As an alternative, dehydration of the butane diol solution, as described above, can be eliminated if the water content of the hydrous butane diol solution is relatively low and/or the purity requirements for the tetrahydrofuran product are selected correspondingly or the (after)purification stage for the tetrahydrofuran raw product is adapted correspondingly. The distillation column K1 illustrated in the FIGURE can also be operated at a temperature—the temperatures in this case may be between 120 and 150° C.—which permits a partial water separation from the hydrous butane diol solution to the desired contents in one stage.

By way of line 7, the hydrous butane diol solution is fed to a packed-bed reactor R. In this reactor R, an acidic aluminum oxide catalyst is arranged over which the hydrous butane diol solution is dehydrated. Catalyst selectivity is increased by the presence of water in the butane diol in comparison to an anhydrous butane diol.

After dehydration has taken place, by way of line 8, a high-tetrahydrofuran fraction is drawn from the packed-bed reactor R. Depending on the desired degree of purity of the tetrahydrofuran product, this high-tetrahydrofuran fraction is distilled in one or several stages. This one-stage or multi-stage distillation process is illustrated by the distillation column K2 shown in the FIGURE. Before the one-stage or multi-stage distillation process, the high-tetrahydrofuran fraction, as a rule, is cooled first, which can take place, for example, in the heat exchange with the cooled heating medium(s) which previously had flowed through the heat exchanger(s) W1 and/or W2.

Summarizing, the advantages of the process according to the invention and of the arrangement according to the invention will be explained again:

On the whole, fewer distillation columns are required so that investment and operating costs are lowered.

The losses caused by thermal stress within the required distillation columns are also reduced which results in a higher yield of tetrahydrofuran.

During dehydration, the process has better selectivity which also leads to an increase in the yield of tetrahydrofuran.

Since no losses of catalyst material occur, there are neither environmental protection nor disposal problems.

Since dehydration takes place under a normal pressure, a concentration of the hydrous butane diol solution on the one hand and, a lay-out of the reactor with respect to an excess pressure, on the other hand, is unnecessary.

No corrosion problems occur and so the reactor does not require a special lining.

By means of the process implementation according to the invention, the dehydration of a hydrous butane diol solution to tetrahydrofuran can be carried out by means of stable, regeneratable and relatively low-cost, acidic aluminum oxide catalysts.

EXAMPLE

Dehydration of Butane Diol Raw Product

Reaction conditions:
　Temperature T=150° C.
Pressure p approx. 1 bar
Catalyst: $Al_2O_3$, medium grain size 0.8 mm LHSV=5 $l/l_{cat}h$
Charge:
　Butane diol raw product, approx. 3.6 mol BAD/l
Conversion: approx. 100%
Selectivity$_{THF}$: approx. 100%

We claim:

1. A process for producing tetrahydrofuran from a hydrous butane diol solution contaminated by light volatile organic compounds, comprising:
   a) removing the light volatile organic compounds in the hydrous butane diol solution by distillation;
   b) removing water from the hydrous butane diol solution to a water content of 2 to 70% by weight water;
   c) dehydrating the thus prepurified hydrous butane diol solution over an acidic aluminum oxide catalyst to produce a high tetrahydrofuran fraction; and
   d) distilling the high tetrahydrofuran fraction in at least one stage to obtain pure tetrahydrofuran.

2. The process for producing tetrahydrofuran according to claim 1, wherein the hydrous butane diol solution contaminated by light volatile organic compounds contains a range of from greater than 2% to 95% by weight $H_2O$.

3. The process for producing tetrahydrofuran according to claim 2, wherein the hydrous butane diol solution contaminated by light volatile organic compounds contains 10 to 90% by weight $H_2O$.

4. The process for producing tetrahydrofuran according to claim 2, wherein the hydrous butane diol solution contaminated by light volatile organic compounds contains 40 to 70% by weight $H_2O$.

5. The process for producing tetrahydrofuran according to claim 1, wherein step (a) takes place at an essentially normal pressure and at a temperature of from 70 to 150° C.

6. The process for producing tetrahydrofuran according to claim 5, wherein step (a) takes place at a temperature of from 90 to 120° C.

7. The process according to claim 1, wherein step (b) produces a water content from 2 to 10% by weight water.

8. An arrangement for producing tetrahydrofuran from a hydrous butane diol solution contaminated by light volatile organic compounds, comprising:
   a) at least one distillation column for removing the light volatile organic compounds from the hydrous butane diol solution;
   b) a reactor connected behind the at least one distillation column in which the hydrous butane diol solution is dehydrated to form a high-tetrahydrofuran fraction; and c) an after purification system comprising at least one stage in which the high-tetrahydrofuran fraction is distilled to form pure tetrahydrofuran.

9. The arrangement according to claim 8, wherein the reactor is a packed bed reactor.

10. The arrangement according to claim 8, further comprising at least one heat exchanger connected in front of the reactor used for heating hydrous diol solution.

11. The arrangement according to claim 6, wherein at least one distillation column is designed as an essentially normal-pressure column and is operated at a temperature range of between 70° C. and 150° C.

12. The arrangement according to claim 11, wherein the essentially normal-pressure column is operated at a temperature range of between 90° C. and 150° C.

13. The arrangement according to claim 8, wherein the reactor contains an acidic aluminum oxide catalyst.

\* \* \* \* \*